United States Patent [19]
Padilla, Jr.

[11] Patent Number: 5,832,928
[45] Date of Patent: Nov. 10, 1998

[54] INTRAVENOUS SITE PROTECTION DEVICE

[76] Inventor: James D. Padilla, Jr., 105A S. Front St., Wilmington, N.C. 28401

[21] Appl. No.: 838,309

[22] Filed: Apr. 8, 1997

[51] Int. Cl.$^6$ ........................................................ A61F 5/37
[52] U.S. Cl. ...................... 128/877; 128/878; 128/DIG. 6
[58] Field of Search ..................... 128/846, 877, 128/878, 879, 888, DIG. 6, DIG. 26; 604/179, 180

[56] References Cited

U.S. PATENT DOCUMENTS

| | | | |
|---|---|---|---|
| 2,693,794 | 11/1954 | Neville | 128/DIG. 6 |
| 3,724,456 | 4/1973 | Waxman | 128/133 |
| 4,502,477 | 3/1985 | Lewis | 128/133 |
| 4,561,857 | 12/1985 | Sacks | 128/DIG. 6 |
| 4,633,863 | 1/1987 | Filips | 128/877 |
| 4,796,611 | 1/1989 | Wardlaw | 128/87 |
| 4,870,976 | 10/1989 | Denny | 128/888 |
| 5,025,801 | 6/1991 | Callaway | 128/877 |
| 5,116,324 | 5/1992 | Brierley et al. | 604/180 |
| 5,238,010 | 8/1993 | Grabenkort | 128/888 |

*Primary Examiner*—Michael A. Brown

[57] ABSTRACT

An intravenous site protection device is formed with a rigid, elongated top member and a rigid, elongated bottom member which are oppositely secured on a patient's extremities. The top member is configured to accommodate a catheter and supply tubing to prevent accidental dislodgement during transportation or movement of the patient. Securing straps maintain the top and bottom members against the extremity of the wearer and a resilient sponge is positioned beneath the top member, against the wearer's skin, to assure proper circulation to the intravenous site. The rigid plastic ensures protection of the intravenous site should the site be struck or contacted with clothing or other articles during intravenous fluid transfer. The preferred form of the invention is made from a transparent plastic to allow ease in monitoring by medical personnel.

5 Claims, 3 Drawing Sheets

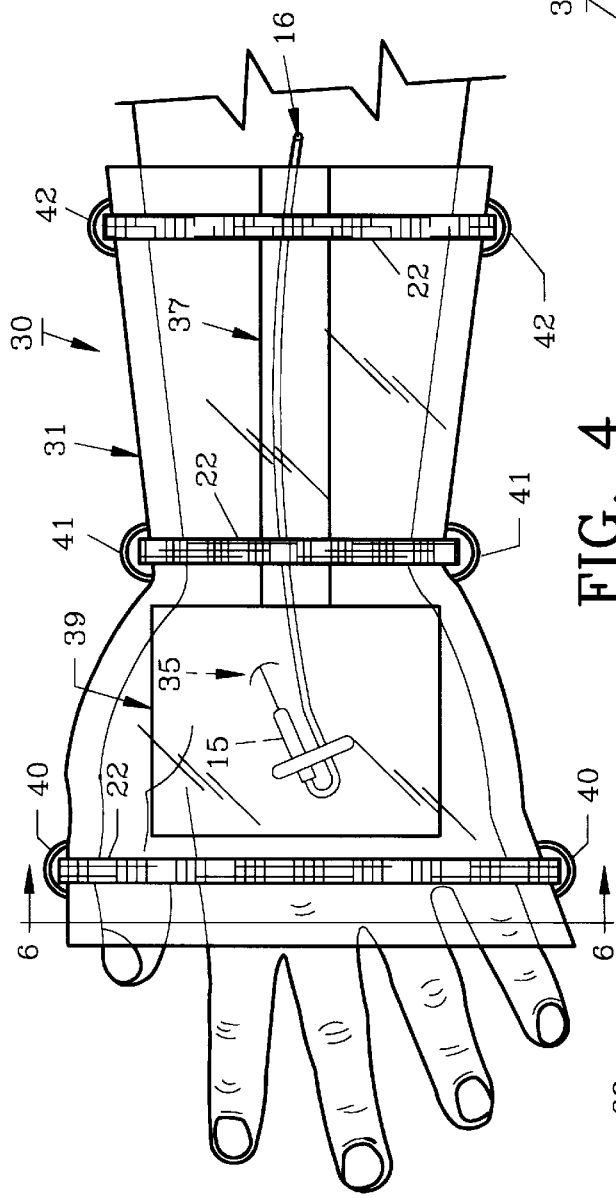
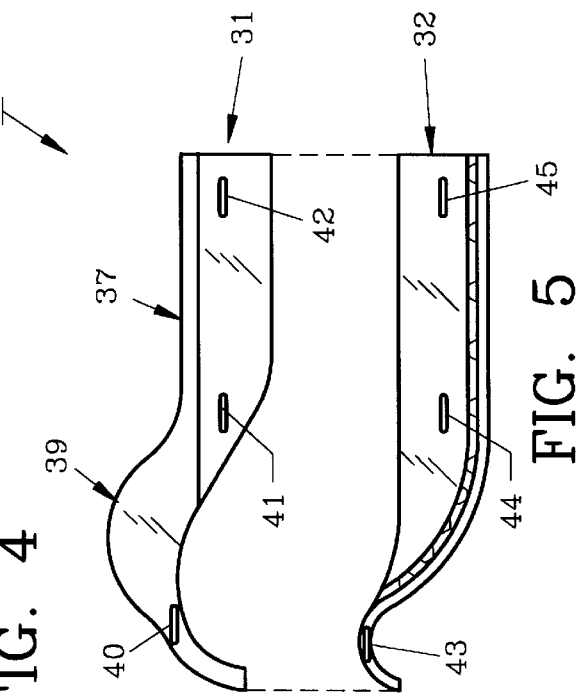
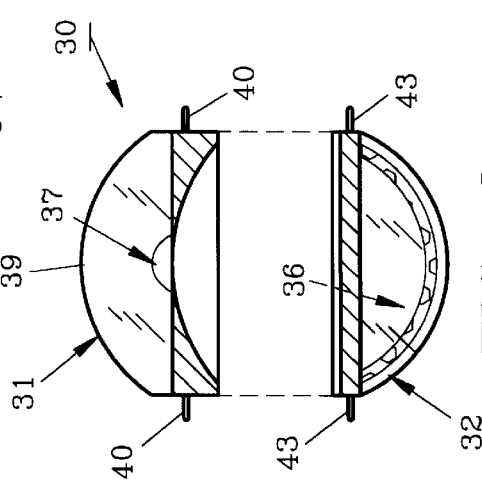

INTRAVENOUS SITE PROTECTION DEVICE

BACKGROUND OF THE INVENTION

1. Field of the Invention

The invention herein pertains to protection of extremity intravenous sites as used by medical personnel and in particular to devices that are used to protect intravenous sites from contact and injury.

2. Description of the Prior Art and Objectives of the Invention

Catheters having fluid tubes attached thereto are used at selected intravenous sites on limbs of patients for supplying blood, saline solutions, medicines and other liquids. Oftentimes patients receiving intravenous therapy must be transported such as from an accident location to a local hospital as quickly and efficiently as possible. Frequently, lifting and moving such a patient will jostle or impact the patient, causing partial or complete removal of the catheter, sometimes with extreme consequences to the patient. At other times a hospital patient receiving intravenous therapy may randomly move or jerk, causing the catheter to withdraw. At other times, the intravenous site on the patient's arm, hand, foot or leg may be brushed with bed coverings, clothing or other items dislodging the catheter and terminating critical intravenous therapy.

Various intravenous protection devices have been developed in the past, such as set forth in U.S. Pat. No. 5,116,324 which discloses a transparent shield for on-site protection of an intravenous catheter. Other devices have attempted to immobilize the extremities during intravenous therapy, as set forth in U.S. Pat. Nos. 3,724,456, 4,502,477 and 5,025,801. Each of these devices is useful in certain circumstances, however, the need for a comprehensive intravenous site protection device has persisted and it is therefore one objective of the present invention to demonstrate an intravenous site protection device for an extremity which both protects and immobilizes the site from contact and which can be easily removed after termination of the therapy.

It is another objective of the present invention to provide an intravenous site protection device which includes a top member and a bottom member which are held in place on an arm or leg by releasable securing straps.

It is still another objective of the present invention to provide an intravenous site protection device which is molded from a rigid, transparent plastic for easy monitoring by hospital medical staff members and emergency medical personnel during patient transportation.

It is a further objective of the present invention to provide an intravenous site protection device which includes a raised portion and connecting channel to accommodate an intravenous catheter and supply tube.

Various other objectives and advantages of the present invention will become apparent to those skilled in the art as a more detailed description is set forth below.

SUMMARY OF THE INVENTION

The aforesaid and other objectives are realized by providing an intravenous site protection device with, in the preferred embodiment, an elongated, transparent, rigid top member having an arcuate cross-section and an elongated, transparent, rigid bottom member also having an arcuate cross-section to fit opposingly along an extremity such as an arm of a patient. The top member includes a raised portion to accommodate an intravenous catheter and a channel which communicates with the raised member to accommodate a flexible tube for supplying fluid to the intravenous catheter. The top and bottom members are adhered to the patient's arm by a plurality of hook and loop securing straps as formed from Velcro® material which pass through loops joined to the top and bottom members. A bridge formed from a polymeric foam is placed beneath the straps against the patient's skin to ensure proper circulation as the securing straps keep the intravenous site protection device properly in place on the patient's arm.

BRIEF DESCRIPTION OF THE DRAWINGS

FIG. 4 features a first alternate embodiment of the invention in place on a wearer's wrist and hand;

FIG. 5 shows a side view of the invention of FIG. 4 removed from the patient's wrist and hand but without a securing strap, catheter, flexible supply tubing or bridge;

FIG. 6 pictures a cross-sectioned view of the embodiment as shown in FIG. 5 along lines 6—6 but removed from the hand and wrist, and without a strap or bridge;

DETAILED DESCRIPTION OF THE PREFERRED EMBODIMENT AND OPERATION OF THE INVENTION

Figure 1:
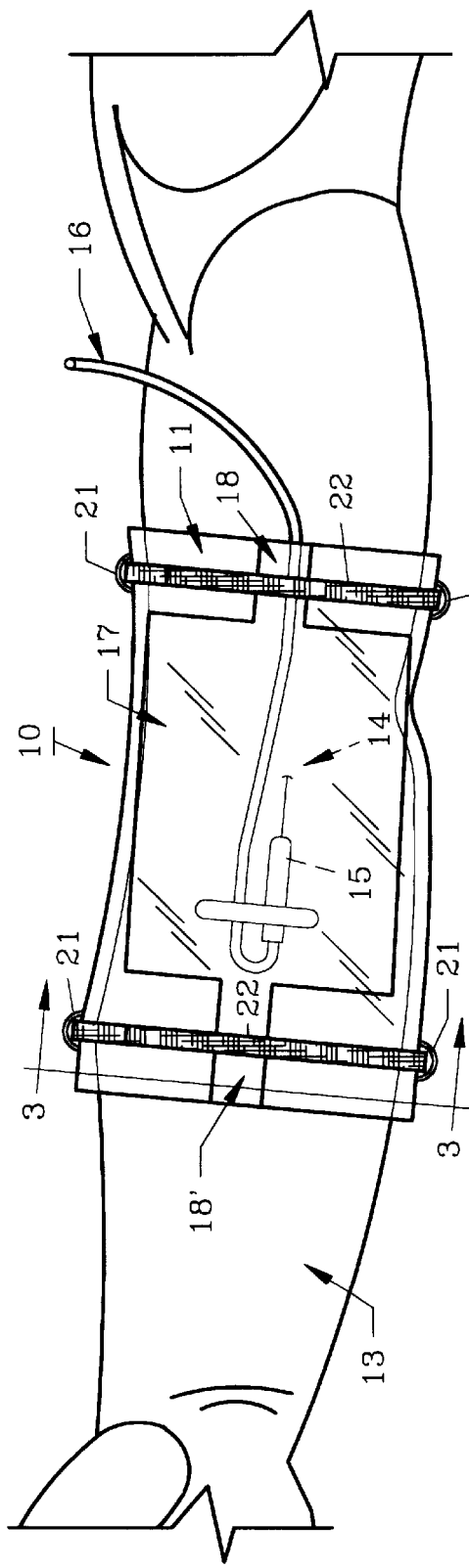
FIG. 1 illustrates a top view of the preferred form of the invention in place on a patient's arm.
Figure 2:
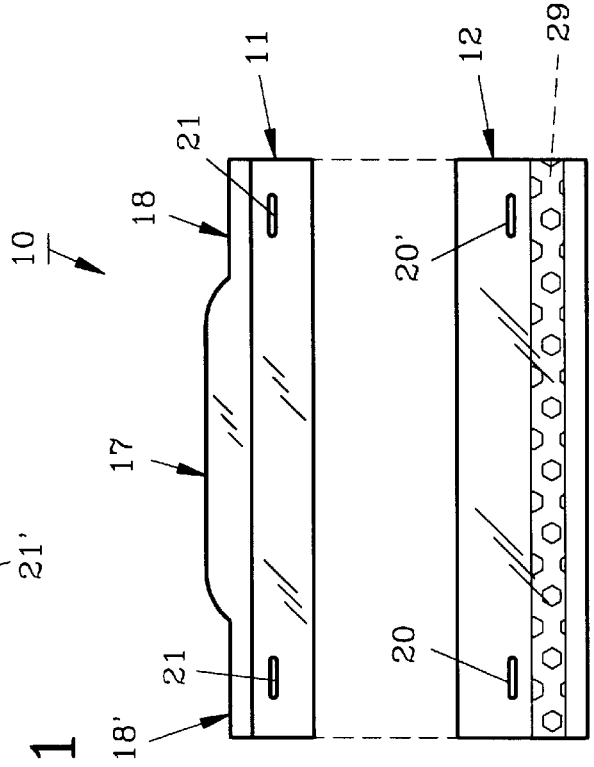
FIG. 2 demonstrates a side view of the device as shown in FIG. 1 as removed from the patient's arm without the securing straps and bridges.
Figure 3:
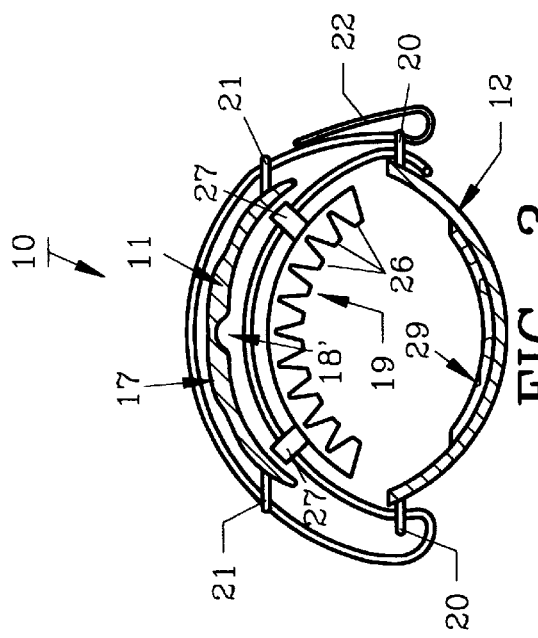
FIG. 3 depicts a cross-sectional view of the device as shown in FIG. 1 along lines 3—3 removed from the patient's arm and includes the bottom member, a loose strap and a bridge joined thereto.

For a better understanding of the invention and its operation, turning now to the drawings, the preferred form of intravenous site protection device 10 is shown in FIGS. 1, 2 and 3 which includes a transparent, elongated, rigid top member 11 having an arcuate transverse cross-section as shown in FIG. 3 and an elongated, rigid arcuate bottom member 12. Top member 11 and bottom member 12 may be formed of suitable polymeric materials such as polyacrylic or polycarbonate plastics which are commercially available and can be molded to the exact size and shape required. For example, various size intravenous site protection devices 10 can be manufactured for infants, small children or small, medium and large adult sizes.

Top member 11 and bottom member 12 are positioned on the wearer's arm 13, as shown in FIG. 1, to protect intravenous site 14 having catheter 15 in place for delivering fluid into patient's arm 13 through supply tube 16. As understood, various medication, or other fluids can be administered through catheter 15 as is standard and usual in medical practice.

In use, a patient's arm is fitted with bottom 12 as shown in FIG. 3 having a moisture absorbing pad, such as cotton pad 29, placed therein. Next, bridges 19 are placed atop the patient's arm proximate strap loops 20, 20' on each side of bottom member 12 also as shown in FIG. 3. Two bridges 19 would be employed with intravenous site protection device 10 as two securing straps 22 are used as seen in FIG. 1. Bridge 19 is formed from a suitably resilient foam material and includes a series of triangular-like legs 26 depending therefrom. Legs 26 contact arm 13 of the patient and are spaced apart to allow optimum blood circulation through the patient's arm under securing straps 22. Bridge 19 includes strap loops 27 as shown in FIG. 3. Thus, with securing strap 22 placed through strap loops 20, it then passes through bridge strap loops 27 as it transverses patient's arm 13 (FIG. 1) where it then passes through loop 20 on the opposite side of bottom member 12. Next, strap 22 passes through loop 21 of top member 11 where it again transverses top member 11 through loop 21 on the opposite side thereof and again through bottom member loop 20 where it is pulled taut and secured to itself. Strap 22 may be formed of a conventional hook and loop fastening material with opposite sides which easily affix to each other. Securing strap 22 may have a width of approximately 15 mm whereas bridge 19 may have a width of approximately 32 mm for adult sizes of intravenous site protection device 10.

As further shown in FIG. 2, top member 11 includes a canopy or raised portion 17 which provides a space between top member 11 and arm 13 to accommodate catheter 15 thereunder. Raised portion 17 allows catheter 15 to operate should arm 13 be accidentally impacted or contacted such as with clothing, or the like. Longitudinal channels 18, 18' are shown in FIGS. 1 and 2 at each end of top member 11 in communication with raised portion 17. Channels 18 and 18' allow intravenous tubing 16 to pass between top member 11 and arm 13 without compression or irritation for connection to catheter 15.

A first alternate embodiment of the invention is shown in FIGS. 4, 5, and 6 whereby intravenous site protection device 30 is shown which includes top member 31 and bottom member 32 as seen in FIGS. 5 and 6. In FIGS. 5 and 6, hook and loop securing straps as previously described are in place to maintain intravenous site protection device 30 along the lower arm, wrist and hand 34 of a patient. As shown in FIG. 4, catheter 15 is in place at intravenous site 35 whereby catheter 15 supplies fluid through intravenous tubing 16 as previously discussed. Intravenous tubing 16 passes through channel 37 as seen in FIGS. 5 and 6 as channel 37 is in communication with raised portion 39. As would be understood, raised portion 39 provides adequate space between top member 31 and intravenous site 35 to allow catheter 15 to be placed therein. As would also be understood, top member 31 provides protection against accidental impact to the wearer's hand which, without intravenous protection device 30 in use, may dislodge catheter 15 or cause other injury.

As further shown in FIGS. 4, 5 and 6, securing straps 22, as earlier described, pass through loop pairs 40, 41 and 42 on top member 31 and through respective lower loops 43, 44 and 45 as shown in FIG. 5 to maintain intravenous site protection device 30 in place on the patient.

Absorbent pad 46 is shown in FIGS. 5 and 6 which consists of a thin layer of cotton fabric or the like to absorb moisture from the patient's skin. Top member 31 and bottom member 32 are maintained in place on the wearer's arm by the use of securing straps 22 which can be conveniently removed as necessary. A bridge to ensure proper circulation, such as bridge 19 shown in FIG. 3, is also employed beneath each of the three (3) securing straps 22 as shown in FIG. 4.

Figure 8:
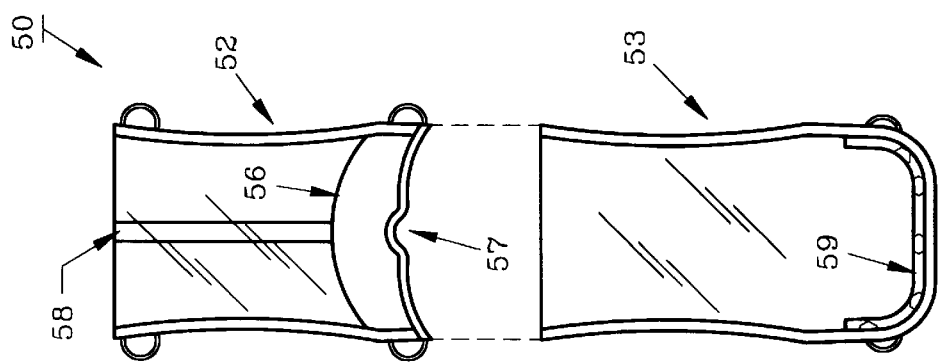
FIG. 8 illustrates the device as shown in FIG. 7 schematically along lines 8—8 with the top member raised for clarity.
Figure 9:
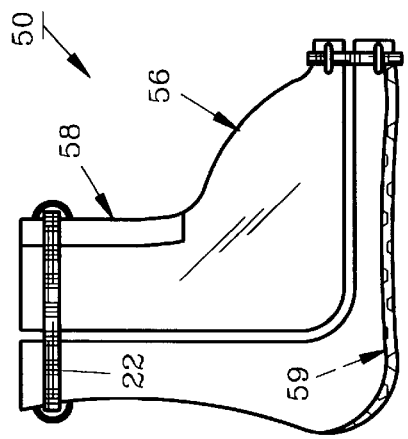
FIG. 9 depicts a side view of the device as shown in FIG. 7 but with the foot removed therefrom.
Figure 7:
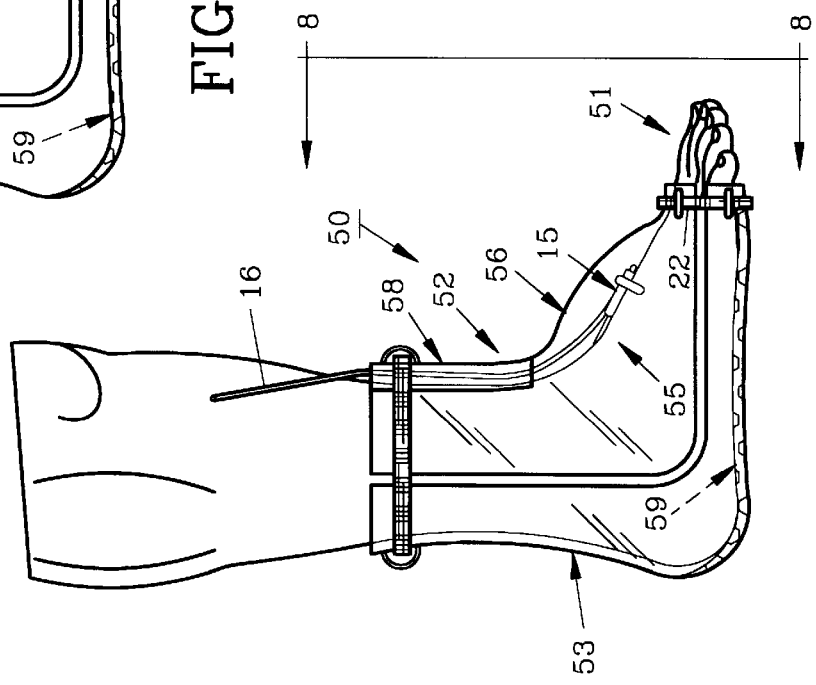
FIG. 7 provides a second alternate embodiment of the invention in place on a patient's foot.

A second alternate embodiment of the invention is shown in FIGS. 7, 8 and 9 whereby intravenous site protection device 50 is shown on patient's foot 51. As seen, rigid, transparent top member 52 is secured to rigid, transparent bottom member 53 by securing straps 22 as hereinbefore described. Catheter 15 with attached needle is in place at intravenous site 55 beneath raised portion 56, as shown in FIGS. 8 and 9. Channels 57 and 58 allow intravenous catheter tubing 16 to conveniently pass thereunder, between the patient's skin and top member 52. Absorbent cotton pad 59, as shown in FIG. 8, absorbs moisture from the patient's foot and provides comfort to the wearer. Securing straps 22 maintain intravenous site protection device 50 and will include bridges 19 as hereinbefore described.

As understood from the embodiments illustrated herein, the invention can be provided in numerous configurations and sizes, depending on the particular site utilized for intravenous fluid delivery. Those skilled in the art may vary the exact embodiments shown herein without departing from the scope of the appended claims, and the illustrations and examples are not intended to limit the protection but are to serve for exemplary purposes.

I claim:

1. A device for protecting an intravenous site on a limb comprising:

a) an elongated rigid top member for covering the limb;

b) a bottom member for placement on the limb opposite to said top member;

c) means for securing said top member to said bottom member, thereby enclosing the limb between said top member and said bottom member; and d) a bridge, said bridge comprising a plurality of spaced apart legs, said legs formed of a resilient material, said bridge disposed between the limb and said top member such that said legs are facing the limb.

2. The device of claim 1 wherein said resilient material comprises a polymeric foam.

3. The device of claim 1 wherein said securing means comprises a strap passing between said bridge and said top member, said strap urged toward the limb during tightening of said strap, whereby said bridge separates said strap and the limb to allow free blood circulation in the limb.

4. The device of claim 1 wherein the device is adapted to fit a human hand.

5. The device of claim 1 wherein the device is adapted to fit a human foot.

* * * * *